US009707073B2

(12) United States Patent (10) Patent No.: US 9,707,073 B2
Al-Jasim (45) Date of Patent: Jul. 18, 2017

(54) PYRAMID-SHAPED BREAST IMPLANT FOR BREAST AUGMENTATION AND/OR BREAST LIFT WITH A METHOD OF USE AND PRODUCTION OF THE SAME

(71) Applicant: Nedaa AbdulGhani Nasif Al-Jasim, Lynnwood, WA (US)

(72) Inventor: Nedaa AbdulGhani Nasif Al-Jasim, Lynnwood, WA (US)

(73) Assignee: Apex Medical Device Design LLC, Lynnwood, WA (US)

( * ) Notice: Subject to any disclaimer, the term of this patent is extended or adjusted under 35 U.S.C. 154(b) by 0 days.

(21) Appl. No.: 14/756,492

(22) Filed: Sep. 5, 2015

(65) Prior Publication Data

US 2017/0065403 A1 Mar. 9, 2017

(51) Int. Cl.
*A61F 2/12* (2006.01)
*B29C 41/08* (2006.01)
*B29K 83/00* (2006.01)
*B29L 31/00* (2006.01)

(52) U.S. Cl.
CPC ........ *A61F 2/12* (2013.01); *A61F 2230/0086* (2013.01); *A61F 2240/004* (2013.01); *A61F 2250/0003* (2013.01); *A61F 2250/0078* (2013.01); *B29C 41/08* (2013.01); *B29K 2083/005* (2013.01); *B29L 2031/7532* (2013.01)

(58) Field of Classification Search
CPC .................................... A61F 2/12; A61F 2/52
USPC ....................................................... 623/7–8
See application file for complete search history.

(56) References Cited

U.S. PATENT DOCUMENTS

| 4,778,465 | A | | 10/1988 | Wilkins | |
|---|---|---|---|---|---|
| 5,112,352 | A | * | 5/1992 | Novack | A61F 2/12 623/8 |
| 5,236,454 | A | | 8/1993 | Miller | |
| 5,480,429 | A | * | 1/1996 | Weber-Unger | A61F 2/52 2/267 |
| 7,105,116 | B2 | | 9/2006 | Bellin et al. | |

(Continued)

FOREIGN PATENT DOCUMENTS

| EP | 2161042 A1 | 3/2010 |
|---|---|---|
| EP | 1515665 B1 | 2/2012 |

OTHER PUBLICATIONS

International Search Report and Written Opinion of the International Searching Authority for PCT Application PCT/US2016/047635 dated Dec. 28, 2016.

(Continued)

*Primary Examiner* — Suzette J Gherbi
(74) *Attorney, Agent, or Firm* — Michael G. Monyok; David G. Oberdick

(57) ABSTRACT

A breast implant device product that mimic the natural pectoral fat pad of the breast and is characterized by an incomplete pyramid with isosceles triangular base and wedge-shaped edges and sloping faces that meet at acute angles with variable degree located medially, laterally and on the top and a footprint characterized by a semicircular lower portion and an oval paraboloid upper portion and a center of gravity located closer to the base than to the profile, the said footprint is advantageously converging and moving towards the underlying surface as the chest wall with a method of manufacturing and a method of use of the said implant including a breast pyramid sizing system.

6 Claims, 8 Drawing Sheets

(56) References Cited

U.S. PATENT DOCUMENTS

| | | | |
|---|---|---|---|
| 2002/0038147 A1* | 3/2002 | Miller, III | A61F 2/12 623/8 |
| 2002/0068972 A1 | 6/2002 | Weber-Unger et al. | |
| 2004/0162613 A1* | 8/2004 | Roballey | A61F 2/12 623/8 |
| 2005/0027307 A1 | 2/2005 | Schwartz et al. | |
| 2005/0149186 A1* | 7/2005 | Roballey | A61F 2/12 623/8 |
| 2006/0282164 A1* | 12/2006 | Seastrom | A61F 2/12 623/8 |
| 2008/0161916 A1* | 7/2008 | Heitman | A61F 2/52 623/7 |
| 2009/0149953 A1* | 6/2009 | Schuessler | A61F 2/12 623/8 |
| 2011/0245921 A1 | 10/2011 | Stelter et al. | |
| 2012/0004723 A1 | 1/2012 | Mortarino et al. | |
| 2012/0226352 A1* | 9/2012 | Becker | A61F 2/12 623/8 |
| 2012/0277860 A1 | 11/2012 | Dvir et al. | |
| 2013/0302510 A1 | 11/2013 | Yu | |
| 2014/0170234 A1 | 6/2014 | Van Epps et al. | |
| 2014/0222146 A1* | 8/2014 | Moses | A61F 2/12 623/8 |
| 2015/0351900 A1* | 12/2015 | Glicksman | A61F 2/12 623/8 |

OTHER PUBLICATIONS

Schwartz, Michael R. "Algorithm and techniques for using Sientra's silicone gel shaped implants in primary and revision breast augmentation." Plastic and Reconstructive Surgery 134, No. 1S (2014): 18S-27S.

Eaves, Felmont F., et al. "Introduction to the Sientra High-Strength Cohesive Gel Implants Supplement." Aesthetic Surgery Journal 35, No. Suppl 1 (2015): S1-S2.

Blondeel, Phillip N., et al. "Shaping the breast in aesthetic and reconstructive breast surgery: an easy three-step principle." Plastic and Reconstructive Surgery 123, No. 2 (2009): 455-462.

Blondeel, Phillip N., et al. "Shaping the breast in aesthetic and reconstructive breast surgery: an easy three-step principle. Part IV—Aesthetic Breast Surgery." Plastic and Reconstructive Surgery 124, No. 2 (2009): 372-382.

Del Yerro, Jose L. Martin, et al. "Selecting the implant height in breast augmentation with anatomical prosthesis: the "number Y"." Plastic and Reconstructive Surgery 131, No. 6 (2013): 1404-1412.

Nickell, William B., et al. "Breast fat and fallacies: more than 100 years of anatomical fantasy." Journal of Human Lactation 21, No. 2 (2005): 126-130.

* cited by examiner

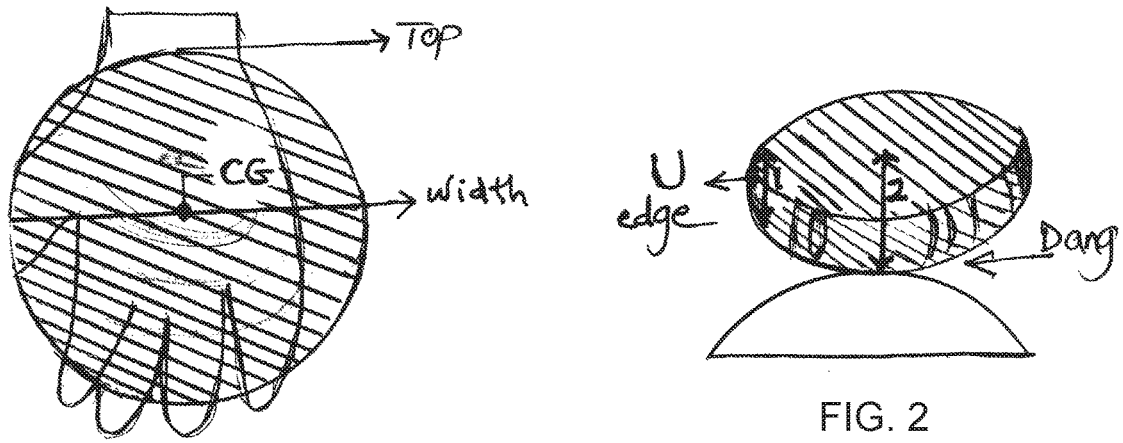
FIG. 1
FIG. 2
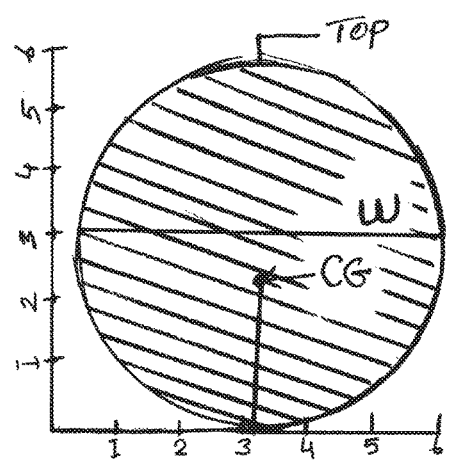
FIG. 3A
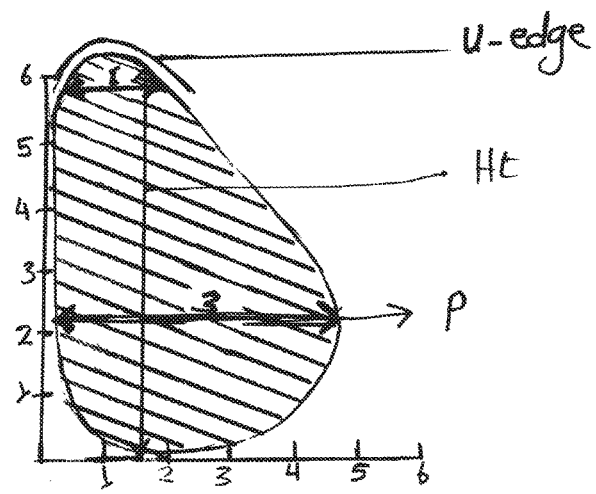
FIG. 3B
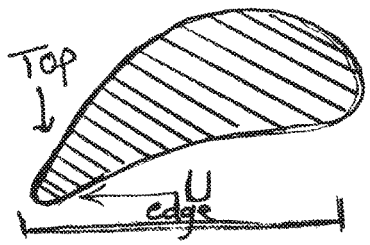
FIG. 4
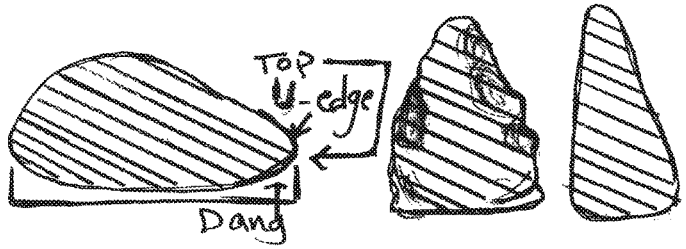
FIG. 5
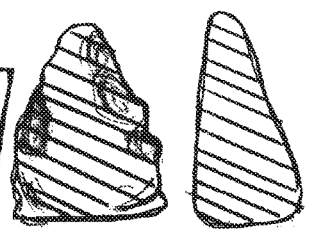
FIG. 6

PYRAMID-SHAPED BREAST IMPLANT FOR BREAST AUGMENTATION AND/OR BREAST LIFT WITH A METHOD OF USE AND PRODUCTION OF THE SAME

TECHNICAL FIELD

The invention is related to the field of human cosmetic and reconstructive breast surgery with a method of manufacturing and method of use including a measurement system of novel pectoral pad breast implant medical device. Breast implant devices are implanted under the breast tissue or under the chest muscle to increase breast size (augmentation) or to rebuild breast tissue after mastectomy (reconstruction). They are also used in revision surgeries, which correct or improve the shape and size of an original surgery or treat complications[1-2]. Breast implants are additionally used in breast lift surgery.

BACKGROUND ART

What are Breast Implant Devices?

Breast implant device is manufactured as an outer shell of silicone elastomer (rubber) distended with a fill that can be either sterile normal saline solution or silicone gel (fourth generation soft silicone, or fifth generation form-stable silicone gel).

Current breast implants are either round-shaped or teardrop-shaped, saline-filled or silicone gel-filled, and they come in a huge combination of width, profile, length and volume. The outer shell can be smooth or textured.

What Concerns does a Breast Augmentation Address?

Breast augmentation and reconstruction surgery aims at restoring the breasts volume and shape that have been lost due to weight loss, lactation, and aging that leave the breast envelop empty and saggy. A breast augmentation address the following most common concerns:

1. Lack of upper pole fullness of the breast
2. Lack of projection of the breast
3. Not enough cleavage
4. Small breasts disproportionately balanced to overall figure

Current SHAPES of Breast Implant

Implant shape is the single most important factor that determines how the new breast will look on the chest postoperatively.

Currently there are only two implant shapes to choose from for surgeons and patients: round- and teardrop-shaped implants that are differentiated by their physical characteristics. The physical characteristics are detailed in the Product Catalogue of the breast implant manufacturers[3-6].

A—Round-Shaped Breast Implant
Physical Characteristics

Is the conventional breast implant used since the sixties, and continue to be the implant of choice to most plastic surgeons. It is shaped like a compressed sphere. The technical goal of this implant is to add volume to the breast. The physical characteristics of round-shaped breast implants are shown in FIGS. 1 and 2, and are the following:

A1—Implant Dimensions (FIG. 1): Have only two dimensions, diameter A, and profile 13
A2—Implant Footprint (FIG. 1, Fp): Have a circular shape
A3—Implant Edges (FIG. 2, Ed): Rounded and thick
A4—Implant edge is moving away (diverging) from the underlying surface (FIG. 1, Dang)
A5—Volume distribution: The four quadrants are similar
A6—"Center of Gravity" (FIG. 1, CG): At the center of the mass of the sphere.

B—Teardrop-Shaped Breast Implant
Physical Characteristics
(Also Called Anatomic, Contoured, Gummy-Bear Breast Implant)

Teardrop implants were introduced recently to the market as a result of innovation in form-stable, highly cohesive, fifth generation silicone gel technology. Originally designed for breast reconstruction after mastectomy, it was designed like a "mature breast". The technical goal of this implant is to concentrate volume on the lower part of the implant with a sloping upper part.

The physical characteristics of teardrop-shaped breast implants are shown in FIGS. 3-6, and are the following:

B1—Implant Dimensions (FIG. 3): Teardrop implant is 3D, with width (A), height (B) and profile (C). There is a constant association between implant dimensions; this is disadvantageous and limiting because:
 a) State-of-art "tall" implants are ONLY 02-1 cm longer than wide
 b) State-of-art "tall" implants are too narrow to fill the breast from side-to-side
 c) "Tall" implant have undesirably big volume.
B2—Implant Footprint (FIG. 3): Sientra implants have circular foot print (FIG. 3, Fp), oval (wider than tall), and the classic that is taller than wide. Other teardrop implants from different manufacturers have a one footprint-fits-all.
B3—Implant Edges (FIG. 4, Ed): Rounded and thick, FIG. 3 demonstrates an example with a profile of 6 centimeters (cm) and an upper pole thickness of 2 cm (arrowed)
B4—Implant edges are moving away (diverging) from the underlying surface (FIG. 5, Dang)
B5—Volume distribution: Concentrated at the implant lower part and poorly filling the breast upper pole
B6—"Center of Gravity" (FIG. 4, CG): Situated low down at the "center of mass"

FIG. 6 demonstrates upright position of the breast implants

Mechanism of Action

The mechanism of filing the breast upper pole is INDIRECT (FIG. 7); both round- and teardrop-shaped implant does not reach up to the upper pole but it increase the breast upper pole by volumizing existing breast tissue low down[7].

Method of Use in Breast Augmentation

Preoperatively. The borders of the breast attachment to the chest wall "breast footprint" is marked as shown in FIG. 8, the upper border is marked at the level of the anterior axillary fold because that is the height of the "implant footprint", the maximum an implant can go up is TWO CENTIMETERS above this level[8-9]. Current description of the breast upper pole does not comply with current.

FIG. 9 shows is an X-ray film of the chest of a patient with breast implant; demonstrate how currently breast implant placement is lowdown on the chest wall similar to a saggy breast.

The best cosmetic results and outer look is obtained when the implant footprint and breast footprints are matching.

Currently there is NO breast implant that can match the recently described upper pole.

Method of Manufacturing of Breast Implants

The process of manufacturing teardrop breast implant is shown in FIG. 10. The mold is inserted in silicone elastomer and then cured to form the shell that gives the implant its shape characteristics. Then the shell is filled by either sterile saline water or by silicone gel (currently fourth and fifth generation form-stable silicone gel are used). The implant shell can be smooth or textured and the volume and dimension are variable.

THE PROBLEM

Clinical Problems Associated with Implant SHAPES

Breast Local Cosmetic Complications

The risk of developing complications after breast augmentation and reconstruction have been studied in extensive clinical trials conducted by implant manufacturers and reviewed by the FDA and other regulatory agencies[8-11]. A group of these complications are referred to as "local breast cosmetic complications". They affect almost all women with breast augmentation and reconstruction surgery with varying degrees, ranging from mild to very sever that requires corrective revision surgery.

It is highly desirable to decrease revision augmentation and reconstruction. The revision surgery occurs in almost 1 in 4 patients. According to the American Society of Plastic Surgeons 2014, revision surgery has been increased 30% for the previous year 2013.

Multiple complications can be combined in one patient (FIGS. 11 and 12). The local breast cosmetic complications include:
A. Visible edges (Ed)
B. Palpable edges
C. Wrinkling/rippling at the upper and medial edges (Ripp)
D. Improper fill of the breast upper pole:
  D1: Round-shaped implants produce bulging upper pole, with an abrupt change (step-off) at the junction of the bulge with the flat chest wall (FIG. 13)
  D2: deficient filling with teardrop-shaped implants (FIG. 14)
E. Lack of proper medial cleavage
F. Gravitational pull (FIG. 15) on breast implants that results in downward displacement of the implant, double bubble appearance, and a saggy breast. FIG. 16 demonstrates the mechanics related to gravitational pull on breast implant; that the larger the horizontal movement of the "center of mass" away from the chest wall, the bigger is the gravitational pull. The horizontal movement of the center of mass, that corresponds to "center of gravity", is directly associated with the implant volume and the volume distribution mostly in the lower implant portion.

Current Solutions for Local Cosmetic Complications

Current solutions for wrinkling, rippling and step-off upper implant end xxx are the following revision SURGICAL procedures:

Change from saline-filled to silicone-filled implants
Go from subglandular placement to submuscular placement to camouflage the implant edges
Go from round-shaped to teardrop-shaped implant
Go for a bigger implant while respecting the breast footprint, the side effects of large implants, but this will increase the risk of further complications
Add acellular dermal matrices at the implant edges to cover rippling and step-off deformity
Add autologous fat grafting Current solutions for LACK of upper pole fullness
Go above the pectoralis major muscle (subglandular placement) because the muscle exert strong pressure on the implant top
Go bigger: by increasing the implant height. The state-of-art "tall implants"
Go round: Round-shaped implants give a better upper pole fullness
Overfill the round-shaped implant, although this will loose the manufacturers warranty
Wear a push-up bra to maintain the shape of the upper pole
Perform a breast lift in addition to augmentation at the same time, to push breast tissue and nipple to restore a higher position of the breast mound. Although the newly reshaped breast is subjected to gravitational pull with time There is NO solution for the gravitational pull on breast implant.

The above-identified solutions camouflage the problem partially but the problem is unsolved; remains to be a concern to women and their partners. Even celebrities, in the best surgical hands, are not spared those complications! The high incidence of revision surgery indicates that there is a huge unmet need in this field.

Breast Foot Print and Breast Upper Pole Dimensions (FIG. 18 is a side view, FIG. 19 is frontal view): The definition of the breast upper pole is not clear. Recent interest in the breast upper pole arises and few scientific papers are published. It can be visualized by holding the breast in the rest of the hand and lifting upward and inward towards the rib cage. Thus we will find that the upper pole extends to about 2 fingers below the clavicle (collarbone). It has been described as oval or paraboloid in shape and is marked by a curved line.

Available anatomical space under the pectoralis major muscle, i.e. submuscular implantation pocket for the breast implant is not filled properly (FIGS. 20 and 21); there is a dead space (empty, nor filled, non-reachable by the implant), located above the implant top and bounded by the pectoralis muscle origin from the collar bone (clavicle); it will be filled with blood and serum with fibrosis (Dead).

Are the Implants Using the Available Anatomic Space Properly?

NO. To use the available anatomical space properly, breast implant footprint should be similar to breast footprint, and this harmonization will result in a naturally looking post-augmentation breast.

My Novel Solution

Disclosure of the Invention

To solve the multitude of local breast cosmetic complications a revolutionary change in the SHAPE of breast implants is mandatory. The technical goal is improve on the shape and minimize or overcome those complications.

The scientific bases of my invention are based on "peeling-off" the layers of the problems with fierce observations on breast anatomy, implant anatomy, and surgical outcomes in breast aesthetic surgery. I was able to pin point the roots of the cosmetic problems; I hypothesize that the rounded edges of the current implants is the root cause of the problems, and since the rounded edges are the outcome of a design based on a sphere or a teardrop; I need to design an implant starting from a triangular pyramid; hence NO rounded edge.

The triangular-pyramid-shaped implant of this invention is anatomy friendly with an idea derived from the natural breast mound shape; when we hold the breast in the rest of the hand an isosceles triangle can be drawn (FIG. 22), and a pyramidal shape can be drawn on this triangular base with a height reaching up to the boundaries of the breast upper pole (FIG. 23). This "breast pyramid" mimics the natural breast "pectoral fat pad" demonstrated in FIG. 17. This makes sense because the pectoral fat pad function is to give breasts their volume, shape, and perkiness. It fills the breast upper pole with a straight slope. Its footprint is a replica of the breast footprint. Accordingly, the breast implant of this invention will inherent all the above-mentioned advantageous characteristics of the pectoral fat pad; be placed behind the pectoral fat pad to add volume and restore shape and function "to pad" the said pectoral fat pad; be named "pectoral-pad" implant.

Physical Characteristics of Pectoral-Pad Breast Implant

1—Implant Dimensions (FIG. 24): Pectoral-pad implant is 3D having height, width, and profile known in the art that is part of the normal human anatomical dimensions. If we first draw a vertical line with a length of 3X, then we intersect the vertical line by a transverse line that divide it into upper ⅔ and lower ⅓, this intersection represents the center of mass and is also the center of gravity, and the position of the nipple areolar complex. The width that is suitable may be 1X+5 centimeters. The profile can be determined independent on the other dimensions.

2—Implant Footprint (FIG. 26): characterized by lower semicircular part and unique upper oblong (oval, or paraboloid) shape that can extend to reach to fill the whole breast footprint. This is possible because we discontinue (break) the constant association of the implant dimension in selecting a pyramid shape, the length can extend without compromising the width (customized implant). The tall sloping upper portion of the implant is reaching high to the upper margin of the breast footprint and thus preventing the step-off deformity of the upper pole 3—Wedge-shaped edges (FIGS. 24, We and 25, We): The pectoral-pad implant is characterized by wedge-shaped upper, medial, and lateral edges that have the following advantages: 3a—Can be pushed "to-the-point" under the pectoralis muscle origins narrow angles, that are located at the periphery of the implantation pocket hence fill the anatomically available space properly, 3b—the wedge slopes gradually to the surrounding chest well and is impalpable and invisible, 3c—the wedge is most likely ripple-proof.

4—Implant edge is moving toward (converging) the underlying surface (FIGS. 24, Cang and 25, Cang) because the implant edges are thin and relaxed 5—Volume distribution: Pectoral pad implant is characterized by unique volume distribution; said triangular pyramid mold shape is further sculptured to resemble the human hand, with a rounded palm area having 55% of the total volume to be placed behind the nipple-areolar complex with 2 lateral wings with a volume of 20% of the total volume, and an upper extension with a volume of 25% of the total volume. This volume distribution can be varied according to the 45/55 percent ratio guidelines and the normal volume distribution of the human population. This volume distribution will allow proper filling of the breast upper pole (i.e., no bulging, no step-off, and no deficiency). The lateral axillary wing can be separated from the main implant body similar to a thumb to extend to the axillary area when required by the patient anatomy. The percentage of distribution can be varied and customized to the patient's need. This volume distribution can be achieved through internal septa or by the form-stable fifth generation silicone gel 6—Center of Gravity (FIG. 26, CG): Pectoral-pad breast implant is characterized as "defy gravity" implant due to the fact that the volume distribution make the center of mass to behave like the small implant of FIG. 16 that is characterized by a short distance between the center of mass and the chest wall, resulting in a small gravitational force. This thin central portion makes surgical support of the implant at the inframammary fold possible to give pectoral-pad implant further defy-gravity characteristic 7—Additional unique feature of pectoral-pad implant is a customized variable acute medial angle (FIG. 27) for placement at the medial cleavage line, with a degree ranging between 80°-45° to provide the desired cleavage by reaching to the origins of intact pectoral muscle origins from the sternum (breast bone)

BEST MODE OF CARRYING OUT THE INVENTION

The method of use of pectoral pad breast implant device consist of multiple steps:

I. Preoperative Implant Sizing:

A unique formula for calculating the volume of the Pectoral-Pad breast implant preoperative size selection, I name it as "Breast Pyramid System". This measurement system is based on the breast triangle and breast pyramid of FIGS. 22 and 23. The formula for calculation is as follows: the surface area of the breast triangle X height of the breast pyramid. If we want to apply the upper pole volume/lower pole volume of 45/55 ratio guidelines, we have to measure the existing breast volume using conventional methods known in the art, then we calculate the formula as:

Upper total volume=the volume of the existing breast tissue above the nipple line+the volume of the upper portion of Pectoral-Pad implant above a line of the center of mass Lower total volume=the volume of the existing breast tissue below the nipple line+the volume of the lower portion of Pectoral-Pad implant below a line of the center of mass Then we select an implant size and proportions that can give the 45/55 ratio II. Implant Surgical Placement:
- As known in the surgical art, the point that the center of mass needs to be placed behind the nipple areolar complex need to be clarified.
- FIG. 28: Demonstrate a direct mechanism of upper breast fill characteristic of this invention.

III. Measuring the Clinical Outcomes of Surgery:
- A. Changes in bra cup size using Pectoral-Pad breast implant (known in the art)
- B. Increase in bust circumference using Pectoral-Pad breast implant (known in the art)
- C. Increase in upper pole measurement using Pectoral-Pad breast implant (unique outcome)

Data Shown in Annex I

Example of Proof of Concept Design Testing

FIG. 29: Comparing Pectoral Pad implant to commercial round-shaped sizer to demonstrate the advantage of going longer.

FIG. 30: Demonstrate Model trying on 350 cc Pectoral-Pad implant with perky full volume breast and straight upper pole line. The thin relaxed pectoral-pad implant upper edge is visible FIG. 31: Model with cup B breast, wearing cup D bra, implant off FIG. 32: Model trying on 350 cc pectoral-pad implant showing that the implant fills cup D bra perfectly; the patient is gaining 2 cup sized. Also, an attractive medial cleavage and gradually slopping upper pole fullness are shown FIG. 33: Model trying 350 cc Pectoral-Pad implant on both sides with gradual contouring, adequate upper pole fullness, attractive medial cleavage and no visible edges the implant is smoothly meeting the surrounding tissues.

INDUSTRIAL APPLICABILITY

This invention is forming the basis of manufacturing novel Pectoral-Pad breast implant device for medical use in breast aesthetic surgery for primary breast augmentation, primary breast reconstruction, revision surgeries to correct complications and improve shape or size, and in breast lift surgery. The "Method of Manufacturing" Pectoral-Pad breast implant includes the following steps:
1—Manufacturing a Pectoral-Pad mold for the manufacturing of the implant shell, the said mold is characterized by being shaped like an incomplete isosceles triangular pyramid sculptured to mimic the natural pectoral fat pad, and is characterized by wedge-shaped edges, acute angles, and a footprint with semicircular bottom portion and oval paraboloid top portion, and sloped surfaces, with or without partitions.
2—Immersing the said mold in silicone elastomer (rubber) and curing it according to the methods known in the art to form the implant shape with the characteristic physical properties.
3—Adding valves to the said Pectoral-Pad mold used to fill the shell with either sterile normal saline water or the fourth or fifth generation silicone gel, the said valve can be single or multiple to fill different compartments selective volumes.

BRIEF DESCRIPTION OF DRAWINGS

FIG. 1: Current round-shaped breast implant top view depicting the center of gravity (CG) and the footprint (FP), the implant fill distribution results in thick periphery and thick center.

FIG. 2: Current round-shaped breast implant lateral view depicting the faulty design having rounded, thick, U-shaped upper edge (U-edge), implant fill distribution results in thick periphery and thick center in a proportion o ½, also depicting diverging angle away from the underlying surface (Dang)

FIGS. 3A-3B: Current Mentor CPG™ Teardrop-shaped breast implant, FIG. 3A depicts a circular footprint (FP) with the center of gravity (CG) positioned below the radius. FIG. 3B is sagittal section of teardrop implant depicting the faulty design having rounded, thick, U-shaped upper edge (U-edge), implant fill is mainly positioned near the bottom and the implant tapers towards the top, but continue to have thick periphery and thick center in a proportion of ⅓.

FIG. 4: Mentor Advanced Memory Gel™ teardrop implant, "the more evolved implant" depicting the same thick, rounded, U-shaped upper edge (U-Edge).

FIG. 5: Mentor CPG memory shape teardrop implant sagittal section depicting diverging angle away from the underlying surface (Dang).

FIG. 6: Depicts improvement of state-of-the-art breast implant highly cohesive "form stable" (on the right) over round moderately cohesive breast implant (on the left) in upright position: collapsed wrinkled upper pole of the round implant.

FIGS. 2 and 3), unrestricted vertical height, linear upper pole slope line, converging angle towards the underlying flat surface (Cang), V-shaped wedged edges (we), and the center of gravity (CG) repositioned inward towards the underlying surface and upward to Defy Gravity (vs. FIGS. 15 and 16).

FIG. 11-14), in-built optimal fill distribution creating lower/upper pole ratio of 45 to 55%, proper placement of the nipple at the implant profile, breast lower pole is shaped into convex smooth contour (vs. FIGS. 13 and 14), thus the outcome is compliant with aesthetic standards set forth by Mallucci 2012.

FIG. 31 is frontal view of the women having cup B breast is wearing desirable cup D bra, FIG. 32 show the same women after inserting 350 cc PectoralPad implant on both bra cups where the inserted implant give her a properly filled bra and resulted in a unique gain of 2 cup sizes.

Figure 7:
FIG. 7: Depicts indirect mechanism of upper breast fill in current breast implants achieved by volumizing the lower breast.
Figure 8:
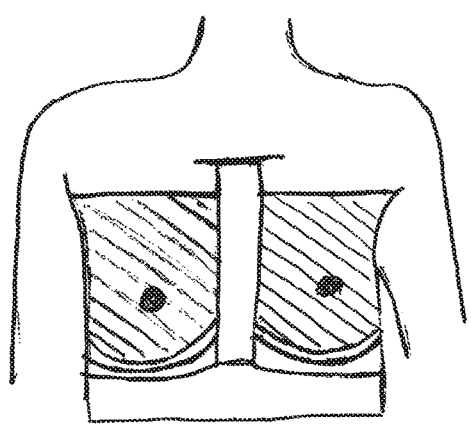
FIG. 8: Current breast footprint is behind the milk glands: preoperative measurements and marking: Upper border at the level of the anterior axillary fold low down on the chest wall (Schwartz 2014) depicting low placement position.
Figure 9:
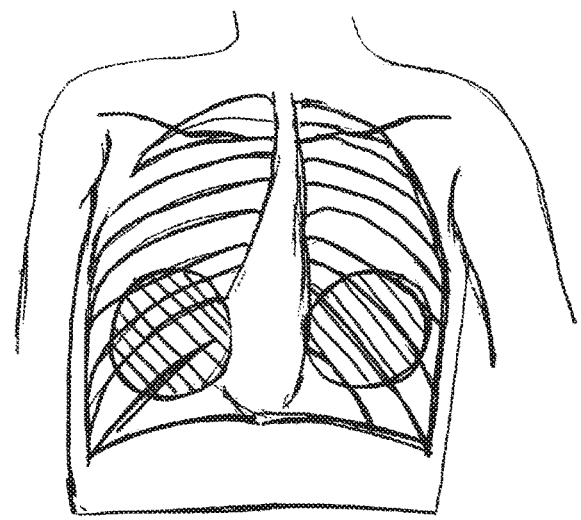
FIG. 9: Chest X-ray of a female with breast implant (implanted female) confirming the low placement position and a ptotic breast appearance.
Figure 10:
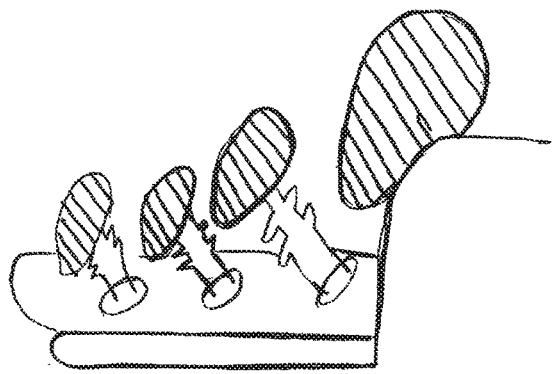
FIG. 10: Method of manufacturing teardrop breast implant depicting a mold (mandrel) having a form that resembles the physical characteristics of the device shell, such a mandrel is intended for use to manufacture an implant shell in one piece by dipping into silicone gel and curing known in the art and described by Polytech Health and Aesthetics in Germany.
Figure 11:
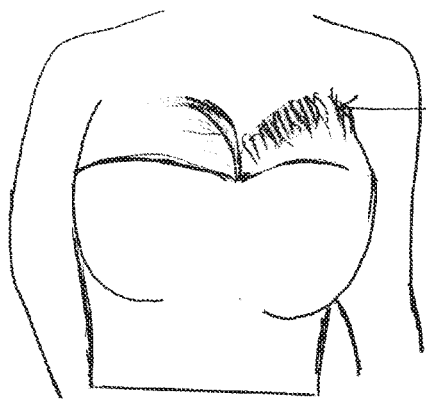
FIG. 11: Depict problems associated with current breast implants, the external appearance of this implanted women depicts multiple cosmetic problems of visible ripples (ripple), and dramatic contour change created between the flat of the upper chest wall and the breast departure point with a step-off bulging upper breast resulted in faked implanted-look.
Figure 12:
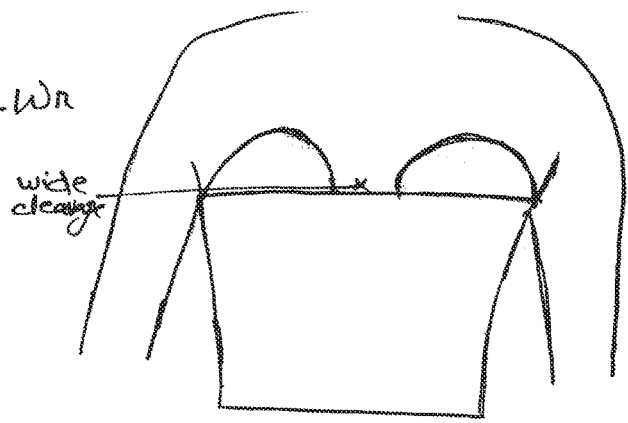
FIG. 12: External appearance of an implanted woman depicting multiple cosmetic problems including wide medial cleavage, bulging breast upper pole with a step-off, and faked-look.
Figure 13:
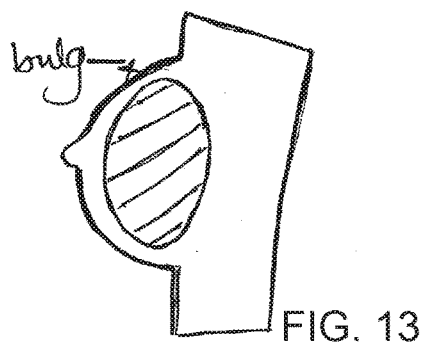
FIG. 13: Lateral view of a breast implanted with a round-shaped implant depicting improperly filled breast upper pole with undesirable fake look, dramatic contour change created between the flat of the upper chest and the point of breast departure (step-off) with a bulging appearance.
Figure 14:
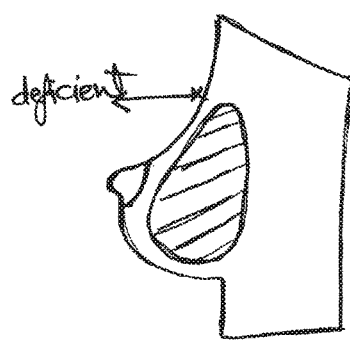
FIG. 14: Lateral view of a breast implanted with a teardrop-shaped implant depicting improperly filled breast upper pole with deficient subtle breast upper pole with major volume positioned at the lower breast pole
Figure 15:
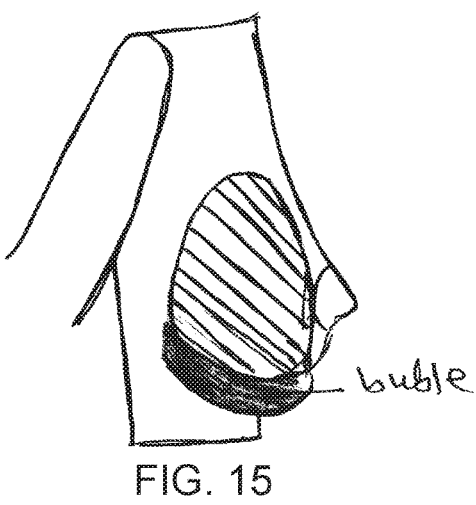
FIG. 15: Lateral view of implanted breast depicting the result of gravitational pull on the implant droopy breast with double-bubble appearance creating unwanted breast distortion.
Figure 16:
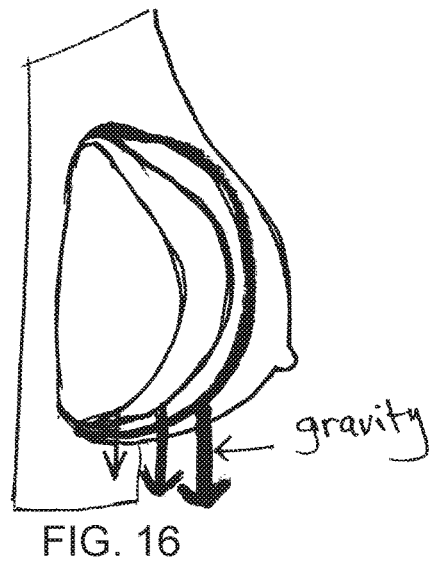
FIG. 16: Depicting that the strength of gravitational pull is proportionate to the implant volume and the distance of the implant "center of gravity" from the chest wall.
Figure 17:
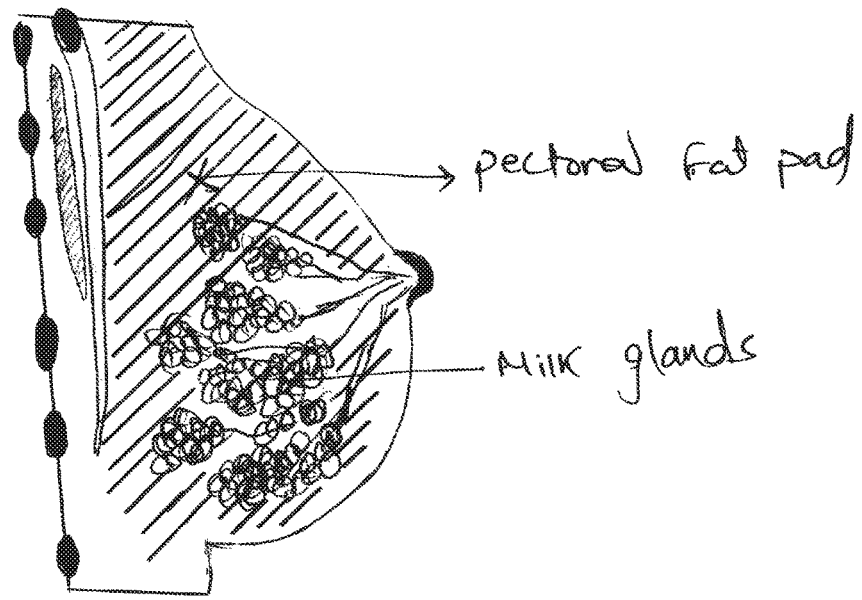
FIG. 17: Aesthetic features of breast anatomy depicting natural breast pectoral fat pad that gives the breast its size and shape, and is mimicked by the implant of this invention.
Figure 18:
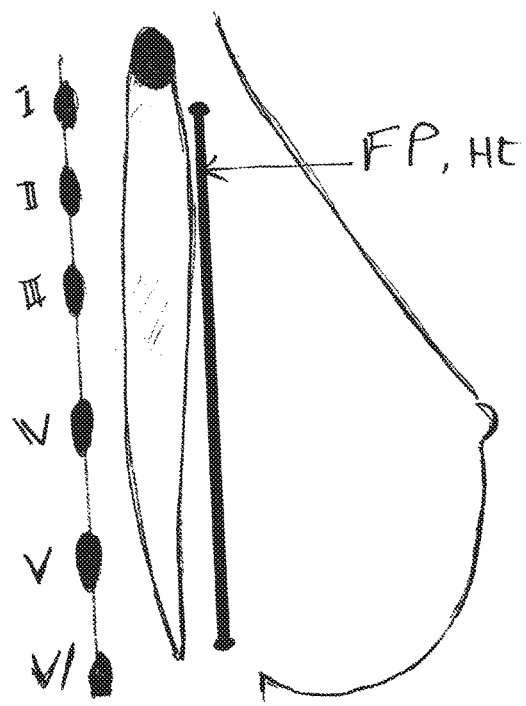
FIG. 18: Recent concepts in breast anatomy depicting natural breast footprint in sagittal section according to Blondeel (2009) with vertical height reaching up to the level of the $2^{nd}$ rib.
Figure 19:
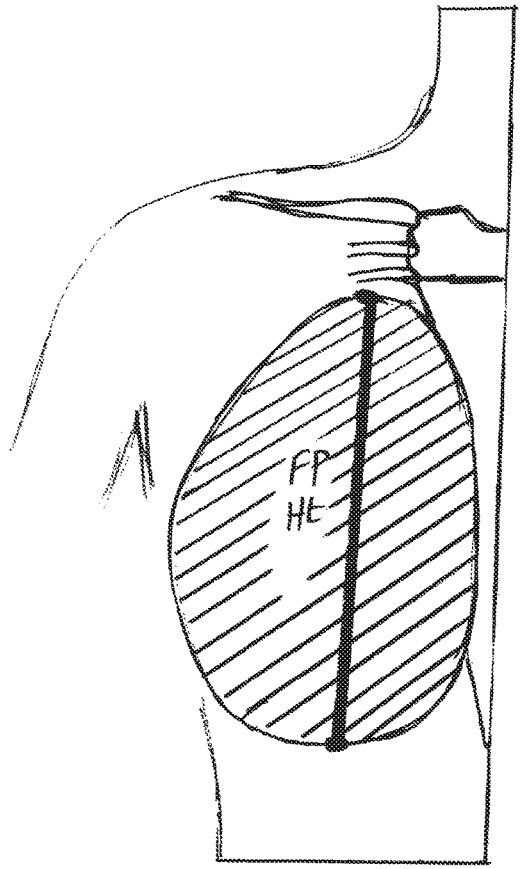
FIG. 19: Recent concepts in breast anatomy depicting the average position and dimension of a paraboloid-shaped breast footprint in frontal view according to Blondeel (2009), this outline form the basis of the foundations on which the breast lies, which is mimicked by the breast implant of this invention.
Figure 20:
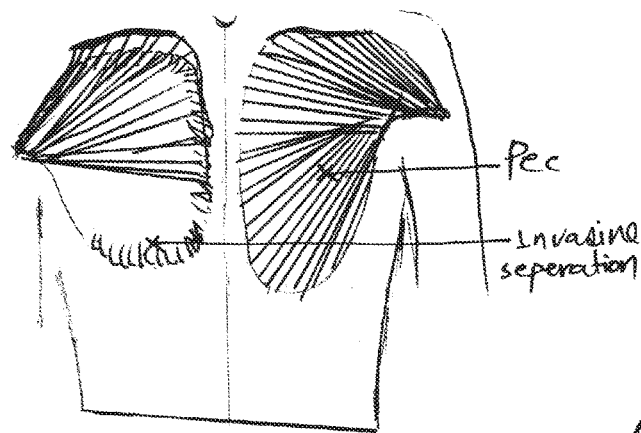
FIG. 20: Current invasive surgical procedure with a primary goal of camouflaging the thick implants edges and accommodate the implant bulk depicting frontal view of pectoralis major muscle origins severed from lower ribs and breastbone.
Figure 21:
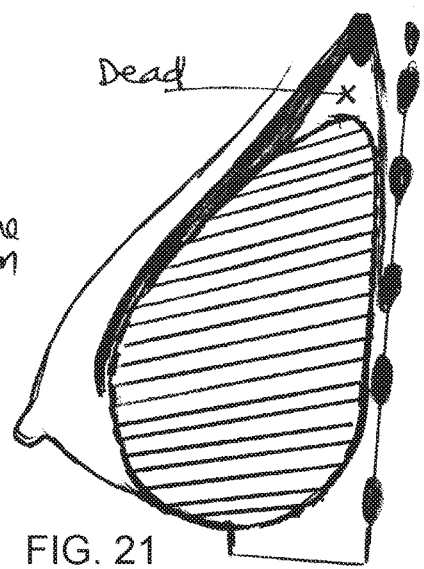
FIG. 21: Current implant physical characteristics are incompatible with its surgical pocket depicting a woman's chest in sagittal section with in-situ teardrop breast implant at submuscular plane, the implant fails to fill the available anatomical space generating a dead space (dead) formed between the U-shaped implant top and the V-shaped pocket apex, the implant is shorter than the pocket, and the nipple (Nip) is not centered on the implant highest point (Profile).
Figure 22:
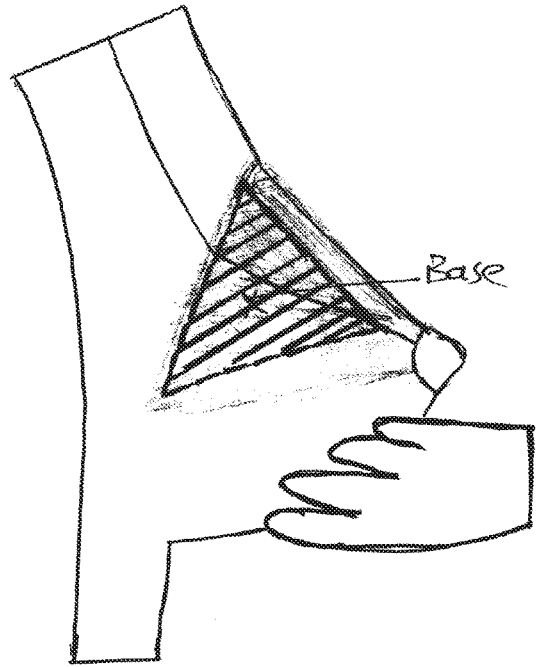
FIG. 22: Shows the first step in designing PectoralPad breast implant of this invention depicting women breast in which the breast was held by the hand and pushed upward until it bends and angled, we draw an isosceles triangular shape with its base lies at the angle, and its plane parallels the upward-facing part of the breast, with the apex pointing to the nipple.
Figure 23:
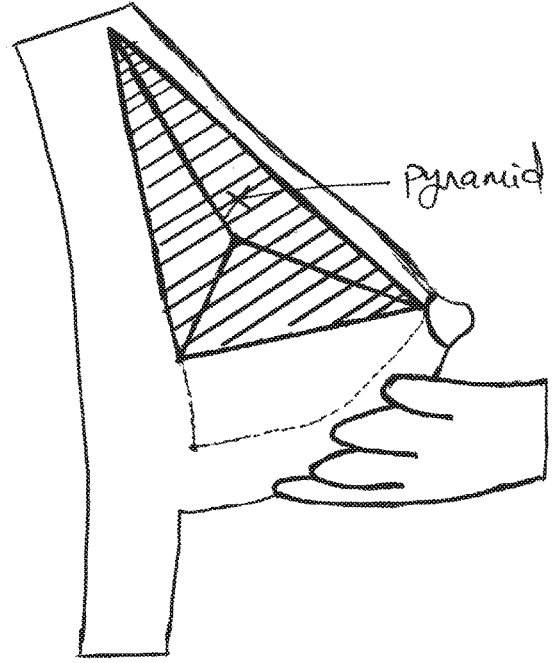
FIG. 23: Shows the second step in designing PectoralPad breast implant was to mark the sternal angle that define the boundaries of the breast footprint (shown in FIGS. 18 and 19)), then complete the drawing of the "breast pyramid" of this invention that will be sculptured to acquire the physical characteristics of the PectoralPad breast implant.
Figure 24:
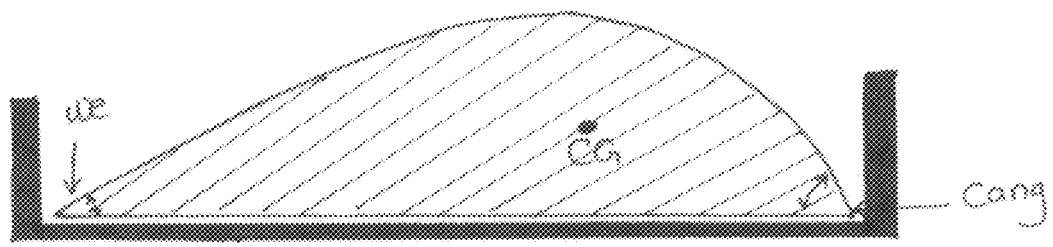
FIG. 24: Physical characteristics of PectoralPad breast implant of this invention in longitudinal section at the middle depicting implant top situated on the left, repositioned implant fill to create an implant characterized by being thin at the periphery thick at the center in a proportion of 1/9 (vs.
Figure 25:
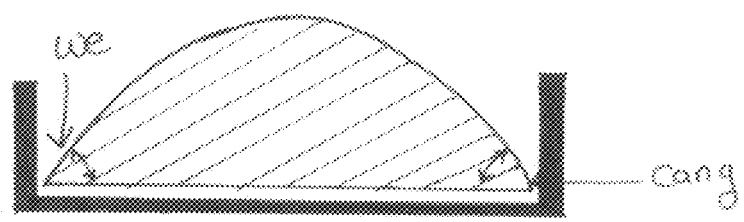
FIG. 25: PectoralPad implant transverse section at the level of the profile (highest point) depicting V-shaped wedged edges (We) with non-identical medial and lateral angles, the implant lies relaxed on the underlying surface resulting in a converging angle (Cang) between the implant footprint and the underlying surface.
Figure 26:
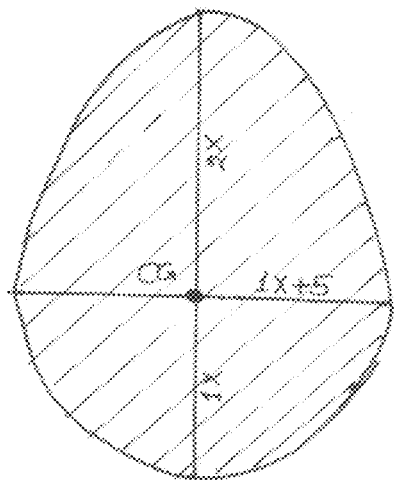
FIG. 26: PectoralPad implant footprint depicting the physical characteristics of paraboloid-shaped base having 3X vertical height, 2X width with the possibility of making it wider by adding a factor (e.g. #5) to customize the implant to a particular women anatomy, and point of intersection representing the location of implant center of gravity (CG).
Figure 27:
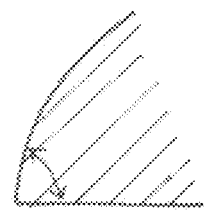
FIG. 27: Partial cross section of the wedge-shaped edge situated on the left of FIG. 25, depicting V-shaped acute angle that can be customized for medial cleavage in a particular patient with a curved boundaries to resemble medial cleavage of the breast.
Figure 28:
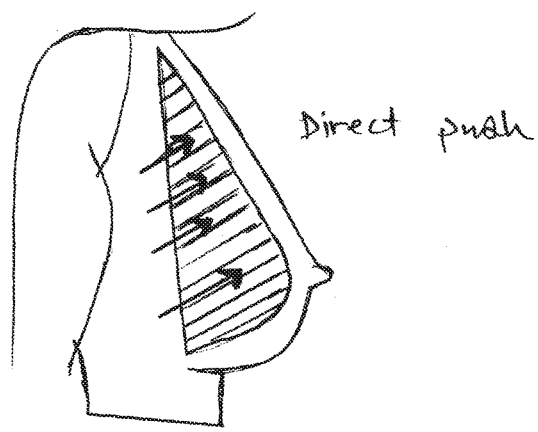
FIG. 28: Breast of implanted women in lateral view depicting the primary functionality of PectoralPad implant that have adequate length to be positioned directly in the upper pole padding and volumizing the hollow skin sac (vs. indirect mechanism of FIG. 7).
Figure 29:
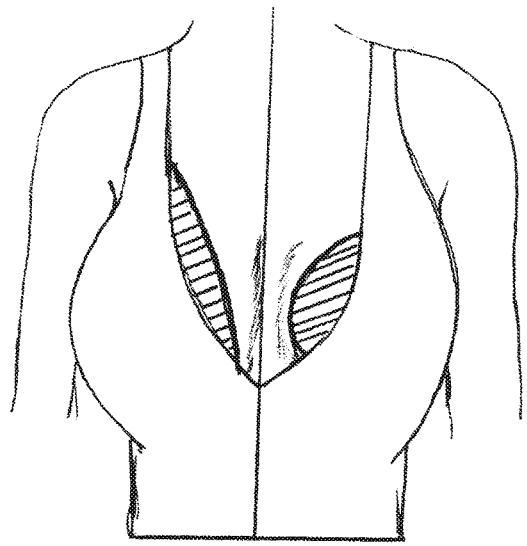
FIG. 29: Comparative study of the functional performance of 300 cc PectoralPad implant inserted over the left breast and commercial 300 cc Purlz sizing breast implant on the right, this frontal view of the chest of implanted women depicts improvement in implant performance resulted from the novel features of PectoralPad implant, evaluation criteria are: 1—Implant vertical height where PectoralPad top reaches the breast footprint top (shown in FIGS. 18 and 19) vs. short Purlz, 2—Breast upper pole (above nipple line) to lower pole ratio of 45:55 can be achieved using PectoralPad implant vs. empty upper pole to bulky lower pole using Purlz, 3—Medial cleavage is narrow, ample and natural looking with PectoralPad vs. wide cleavage with Purlz, 4—Increase in breast size using equal volume in both implants PectoralPad implant make more attractive larger statement breast than Purlz, 5—Suitability of the implant dimensions and shape to breast anatomy PectoralPad give a perky youthful look vs. ½ grapefruit appearance situated on top of glandular tissue.
Figure 30:
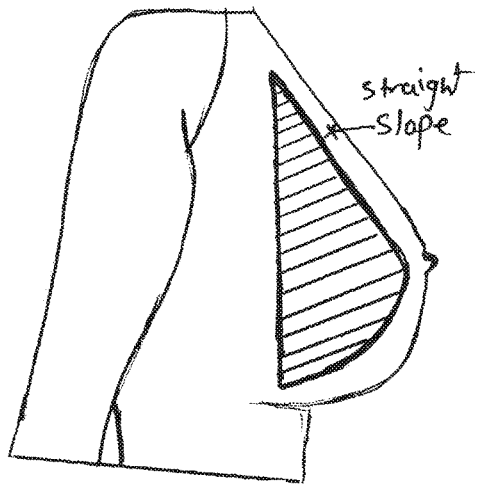
FIG. 30: Avoidance of complications and improved aesthetics of breast upper pole resulting from PectoralPad implant physical characteristics shown in lateral view of breast with inserted 350 cc PectoralPad implant depicting straight slope of breast upper pole formed by the pyramid front edge, no contour breakage at the top where the wedge-shaped edge have a slanted takeoff and smoothly meets the surrounding breast tissues (vs.
Figure 31:
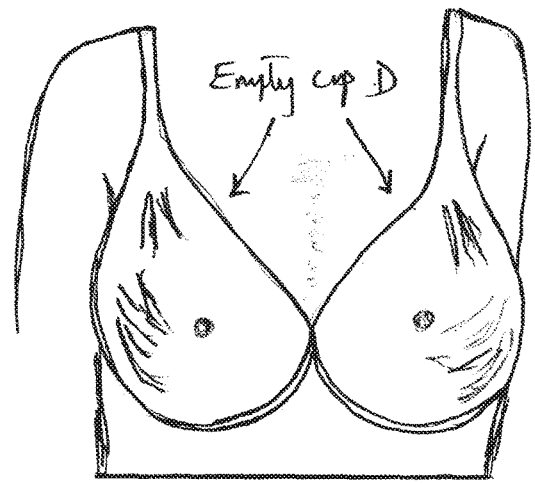
FIGS. 31 and 32: Visualizing the gain in bra cup size resulted from PectoralPad implant.
Figure 32:
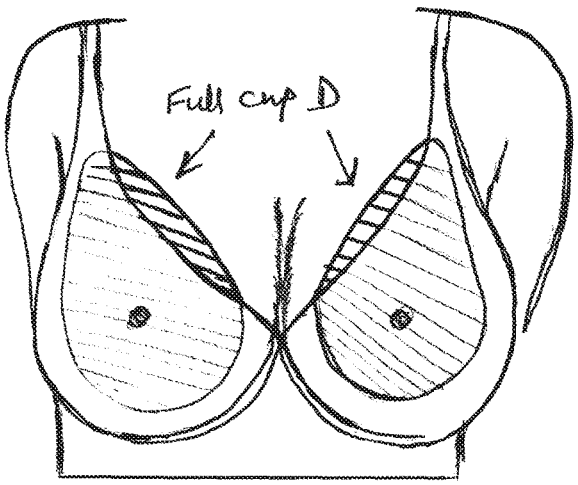
Figure 33:
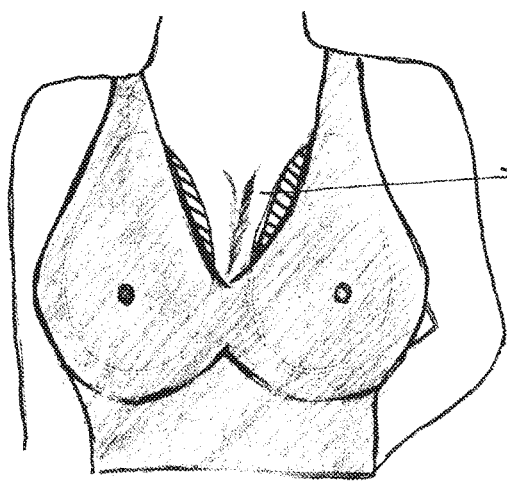
FIG. 33: Superior Pectoralpad implant performance depicting cosmetic outcomes of using PectoralPad implant visualized in chest frontal view of a women, this implanted women is wearing body-tight black top and inserting 350 cc PectoralPad implant on both sides it is noticeable that the implant device is smoothly meeting the surrounding tissue, desirable increase tissue thickness in upper breast (padding), produce ample cleavage, maintain V neckline of the top, make a larger statement and take the breasts to new heights with optimal performance.

The invention claimed is:
1. A breast implant device that mimics the physical characteristics and configuration of natural fatty tissue of the breast comprising:
   a body comprising a volume between a footprint and a front surface, the body having an upper portion and a lower portion, wherein the upper portion of the body comprises a truncated triangular isosceles pyramid sculptured to the shape of the breast above the horizontal level of the nipple, wherein a perimeter of the footprint defined by an edge of the upper portion of the body has an oval paraboloid shape, wherein the front surface has a straight slope, wherein the footprint intersects the front surface to form a wedge-shaped edge, wherein an angle between the footprint and front surface at the edge is acute, wherein the body vertical height is unlinked to its width, wherein the upper portion of the body fills the breast upper pole, wherein the lower portion of the body is a segment of a sphere that fills the lower pole of the breast, wherein a perimeter defined by the edge of the lower portion of the body has a semi-circular shape, wherein the footprint is configured to lie on a chest wall, and wherein a center of gravity of the body is located at the junction of the upper and lower portion of the body closer to the footprint than the front surface.

2. The breast implant device of claim 1 wherein a medial cleavage angle is variable with a range from 20 to 89 degrees.

3. The breast implant device of claim 1, wherein the center of gravity of the body is positioned closer to the footprint than to the front surface, located at the meridian point of the breast triangle.

4. The breast implant device of claim 1 having selective implant fill distribution,
   wherein a volume of a central palm area of the body is about 55% of a total fill volume of the implant body,
   wherein a volume of the upper extension is about 25% of the total fill volume of the implant body, and
   wherein a remaining fill volume of the total is distributed on a medial and lateral wings.

5. The breast implant device of claim 1 having an alternative implant fill distribution wherein 45% of the total fill volume is located above an implant profile line and 55% of the total fill volume is located below the implant profile line.

6. The breast implant device of claim 1 wherein the body comprises a solid pliable silicone gel without a shell.

* * * * *